(12) United States Patent
Xu et al.

(10) Patent No.: US 12,161,294 B2
(45) Date of Patent: Dec. 10, 2024

(54) LARYNGEAL MASK AIRWAY FOR GASTROSCOPY

(71) Applicant: Zhejiang Sungood Technology Co., Ltd., Hangzhou (CN)

(72) Inventors: Penghong Xu, Hangzhou (CN); Yongfeng Wang, Hangzhou (CN); Hongtao Wanyan, Hangzhou (CN)

(73) Assignee: Zhejiang Sungood Technology Co., Ltd., Hangzhou (CN)

( * ) Notice: Subject to any disclaimer, the term of this patent is extended or adjusted under 35 U.S.C. 154(b) by 1252 days.

(21) Appl. No.: 16/870,574

(22) Filed: May 8, 2020

(65) Prior Publication Data

US 2020/0352417 A1   Nov. 12, 2020

(30) Foreign Application Priority Data

May 9, 2019   (CN) .......................... 201910386477.0

(51) Int. Cl.
  *A61B 1/00*   (2006.01)
  *A61B 1/273*   (2006.01)
  *A61M 16/04*   (2006.01)

(52) U.S. Cl.
  CPC ...... *A61B 1/00094* (2013.01); *A61B 1/00082* (2013.01); *A61B 1/00131* (2013.01); *A61B 1/2736* (2013.01); *A61M 16/0409* (2014.02); *A61M 16/0459* (2014.02); *A61M 16/0463* (2013.01); *A61M 16/0479* (2014.02)

(58) Field of Classification Search
  CPC ............ A61B 1/00094; A61B 1/00082; A61B 1/00131; A61B 1/2736; A61B 1/00154; A61B 1/00064; A61M 16/0409; A61M 16/0459; A61M 16/0463; A61M 16/0479; A61M 16/201; A61M 16/0486; A61M 25/1011; A61M 25/10186; A61M 25/10187
  See application file for complete search history.

(56) References Cited

U.S. PATENT DOCUMENTS

| | | | |
|---|---|---|---|
| 2005/0229933 A1* | 10/2005 | McGrail | A61M 16/0484 128/207.14 |
| 2006/0201516 A1* | 9/2006 | Petersen | A61M 16/04 128/207.14 |
| 2011/0237896 A1* | 9/2011 | Black | A61M 16/0486 128/207.15 |

FOREIGN PATENT DOCUMENTS

CN   209301945 U   *   8/2019

\* cited by examiner

*Primary Examiner* — Nathan R Price
*Assistant Examiner* — Fatimata Sahra Diop
(74) *Attorney, Agent, or Firm* — Owen G. Behrens; Smith & Hopen, P.A.

(57) ABSTRACT

A laryngeal mask airway (LMA) for gastroscopy includes a laryngeal tube for gastroscopy. A drainage tube is fixedly installed on an outer surface of an upper end of the laryngeal tube for gastroscopy. A PC connector is fixedly installed at one end of the drainage tube. A ventilation hole is formed in an outer surface of an upper end of the drainage tube, and a suction hole is formed in an outer surface of a lower end of the laryngeal tube for gastroscopy. An inner cavity and an inflation tube hole are formed inside the laryngeal tube for gastroscopy. The inflation tube hole is disposed under the inner cavity and receives an inflation tube, and a single-cavity connector is fixedly installed at one end of the inflation tube. The LMA absorbs secretions from a patient's esophagus to minimize coughing during a gastroscopy, thereby reducing patient discomfort and pain.

9 Claims, 4 Drawing Sheets

LARYNGEAL MASK AIRWAY FOR GASTROSCOPY

CROSS-REFERENCE TO RELATED APPLICATIONS

This nonprovisional application is a continuation of and claims priority to international application No. CN 201910386477.0, entitled "Laryngeal mask airway for gastroscopy," filed May 9, 2019, by the same inventors.

BACKGROUND OF THE INVENTION

1. Field of the Invention

This invention relates, generally, to a laryngeal mask airway (LMA). More specifically, it relates to a LMA used in gastroscopic examination applications.

2. Brief Description of the Prior Art

During endoscopy, it is necessary to insert a gastroscopic catheter through a patient's throat trachea into the patient's stomach. In the process of inserting the catheter, it is often necessary to use some medical equipment to relieve the pain experienced by the patient. For example, an LMA can be used to aid in the insertion of the catheter into the stomach. By using the mask, damage to the throat and tracheal mucosa can be minimized.

However, intubation via existing LMAs is incapable of absorbing the secretions in the upper part of the esophageal opening. In a situation in which the patient chokes and coughs due to the reflux of the upper part of the esophageal opening, the patient experiences pain, because the intubation device is not set in place. Accordingly, what is needed is a laryngeal mask used for intubation and gastroscopic examination, in which a drainage tube and a suction hole are arranged on the LMA to absorb and remove the secretions generated during the gastroscopy, thereby avoiding coughing caused by secretions during gastroscopic procedures. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a laryngeal mask airway configured for use in a gastroscopic procedure is now met by a new, useful, and nonobvious invention.

The novel structure includes a laryngeal tube configured for use during a gastroscopy. The laryngeal tube includes an outer surface, an inner surface, and a sidewall joining the outer surface and the inner surface. The inner surface defines a cavity therein, and the outer surface defines a suction hole. An inflation tube hole is defined within the sidewall. An inflation tube includes a first end received within the inflation tube hole of the laryngeal tube. A second end of the inflation tube is connected to a single-cavity connector. A drainage tube is fixedly secured to the outer surface of the laryngeal tube. The drainage tube includes a first end connected to a physical connection connector unit that is configured to connect the drainage tube to an external monitoring device. The drainage tube defines a ventilation hole within an outer surface thereof. In an embodiment, the drainage tube has a diameter of at least 14 mm. The outer surface of each of the drainage tube and the laryngeal tube may include a hydrophilic coating; similarly, the inner surface of the laryngeal tube and an inner surface of the drainage tube may include a hydrophilic coating.

A large balloon surrounds a middle portion of the laryngeal tube and the drainage tube. A small balloon surrounds an end portion of the laryngeal tube and the draining tube, such that the small balloon is disposed opposite the single-cavity connector. The large balloon, the small balloon, and inflation tube form a closed fluid flow system. In an embodiment, each of the ventilation hole and the suction hole are disposed between the large balloon and the small balloon.

In an embodiment, a sealing belt is secured to each opposing end of the large balloon to secure the large balloon to each of the laryngeal tube and the drainage tube. In an embodiment, a sealing belt is secured to a non-terminal end of the small balloon; the non-terminal end is disposed between a terminal end of the small balloon and the large balloon. The sealing belt configured to secure the small balloon to each of the laryngeal tube and the drainage tube.

In an embodiment, an indication balloon is secured at a first end to a connecting tube, and the connecting tube is received within the inflation tube hole. The indication balloon is secured at a second end to a valve connector, with the valve connector being secured to a one-way valve. The indication balloon is configured to receive an amount of air therein, and the one-way valve is configured to display an amount of air within the system based on the amount of air received within the indication balloon.

The laryngeal tube is configured to receive an airflow therein via the inflation tube to fill each of the large balloon and the small balloon to expand a volume of the laryngeal mask airway to secure the laryngeal mask airway within a patient's esophageal tube. The suction hole is configured to receive secretions from the patient's esophageal tube to minimize patient discomfort. The ventilation hole is configured to remove fluid from the drainage tube.

An object of the invention is to solve the problem that the intubation devices of existing laryngeal masks cannot absorb and clean the secretions in the upper part of the esophagus. As such, there is a problem of patient coughing due to the reflux of the upper part of the esophageal opening during gastroscopy. Accordingly, an object of the invention it to capture or prevent secretions to minimize patient coughing.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1:
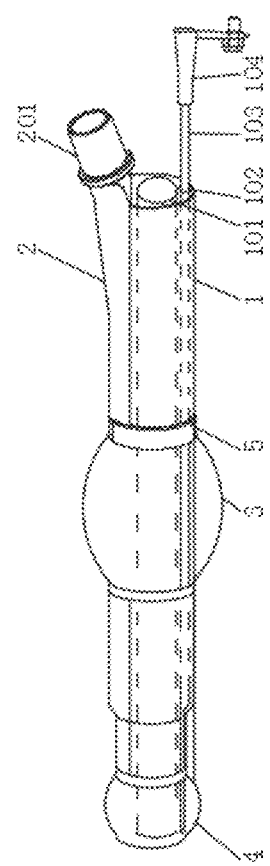
FIG. 1 is a schematic view of a laryngeal mask used in intubation and gastroscopic examination, in accordance with an embodiment of the present invention.
Figure 2:
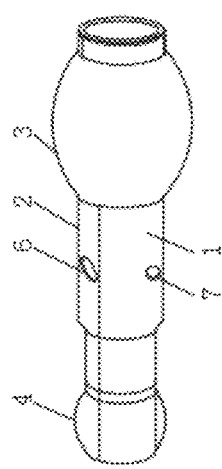
FIG. 2 is a perspective view of a portion of the apparatus of FIG. 1, including a combination of a laryngeal tube for gastroscopy, a ventilation hole, a drainage tube, and a suction hole, in accordance with an embodiment of the present invention.
Figure 3:
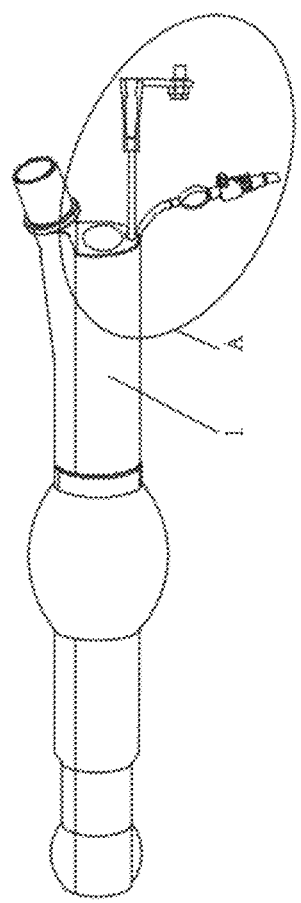
FIG. 3 is a perspective view of the apparatus of FIG. 1, including an indicator balloon attached to the combined laryngeal tube for gastroscopy, ventilation hole, drainage tube, and suction hole shown in FIG. 2.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The present invention includes a laryngeal mask airway (LMA) for gastroscopy, including a laryngeal tube for gastroscopy. A drainage tube is fixedly installed on an outer surface of an upper end of the laryngeal tube for gastroscopy. A PC connector is fixedly installed at one end of the drainage tube. A ventilation hole is formed in an outer surface of an upper end of the drainage tube, and a suction hole is formed in an outer surface of a lower end of the laryngeal tube for gastroscopy. An inner cavity and an inflation tube hole are formed inside the laryngeal tube for gastroscopy. The inflation tube hole is disposed under the inner cavity and receives an inflation tube, and a single-cavity connector is fixedly installed at one end of the inflation tube. The LMA absorbs secretions from a patient's esophagus to minimize coughing during a gastroscopy, thereby reducing patient discomfort and pain. The LMA is discussed in greater detail in the sections below Referring to FIGS. 1-4, an LMA for gastroscopic examination includes a laryngeal tube for gastroscopy 1. A drainage tube 2 is fixedly mounted to the upper surface of the upper end of the laryngeal tube for gastroscopy 1. The drainage tube 2 is usable within the patient's esophagus during the gastroscopic procedure. Specifically, secretions produced by the patient, particularly the patient's mouth, are drained via the drainage tube 2. In an embodiment, the diameter of the drainage tube 2 is at least 14 mm, and since the inside of the drainage tube 2 can receive different types of endoscopes, the diameter of the largest endoscope that can be received within the drainage tube 2 is approximately 13.5 mm. A PC (physical contact) connector 201 is fixedly mounted to one end of the drainage tube 2, such that the PC connector 201 can connect the laryngeal tube for gastroscopy 1 to an external device. In an embodiment, the drainage tube 2 and the outer surface and the inner surface of the laryngeal tube for gastroscopy 1 are coated with a hydrophilic coating. The coating makes the drainage tube 2 and the inner and outer surfaces of the laryngeal tube for gastroscopy 1 more lubricated, facilitating the insertion of the laryngeal mask and the laryngeal tube for gastroscopy 1 into the esophageal tube of the patient.

A ventilation hole 6 is disposed within the outer surface of the upper portion of the drainage tube 2. A suction hole 7 is disposed within the outer surface of the lower portion of the laryngeal tube for gastroscopy 1. The suction hole 7 can absorb and clean secretions, thereby minimizing and preventing the occurrence of patient coughing caused by secretions during the gastroscopy. The ventilation hole 6 is disposed to receive a fiberoptic bronchoscope therein to monitor the breathing of the patient.

The inside of the laryngeal tube for gastroscopy 1 includes a cavity 101 and an inflation tube receipt 102. The cavity 101 enables a cleaning fluid to flow therethrough into the stomach of the patient to clean the stomach during the gastroscopy procedure. The inflation tube insertion receipt 102 is used to receive a first end of an inflation tube 103 therein. The inflation tube receipt 102 is disposed between the cavity 101 and the outer surface of the laryngeal tube for gastroscopy 1. The inflation tube 103 can inflate the large balloon 3 and the small balloon 4, which are connected to the drainage tube 2, and are discussed in greater detail below. A second end of the inflation tube 103 is fixedly mounted to a single-cavity connector 104, and the single-cavity connector 104 can connect the inflation tube 103 to an external inflator.

The large balloon 3 is fixedly mounted to each of the laryngeal tube for gastroscopy 1 and the outer surface of the drainage tube 2 at an intermediary position of each of the laryngeal tube for gastroscopy 1 and drainage tube 2, as particularly shown in FIG. 1. The laryngeal tube for gastroscopy 1 and the outer surface of the drainage tube 2 continue beyond the large balloon 3 to fixedly mount to the small balloon 4, which is disposed at an opposing end of the apparatus as the single-cavity connector 104. The inflated large balloon 3 and the small balloon 4 can be more stably inserted within the esophagus of the patient, thereby providing a more stable placement of the laryngeal tube for gastroscopy 1 within the patient's esophagus and throat. In addition, due to the configuration and connections of the combined apparatus, each of the large balloon 3, the small balloon 4, and the inflation tube 103 are in fluidic communication with each other, so that the inflation tube 103 can inflate each of the large balloon 3 and the small balloon 4.

In addition, the outer surface of both sides of the large balloon 3 and the outer surface of the small balloon 4 disposed proximate to the large balloon 3 are surrounded by a sealing band 5. As such, a closed system is created for fluid flow within the system, and the sealing band 5 minimizes fluid escape from the large balloon 3 and the small balloon 4. Instead, the ventilation hole 6 and the suction hole 7 are disposed between the small balloon 4 and the large balloon 3, as discussed above, for fluid venting and secretion absorption, respectively.

Figure 4:
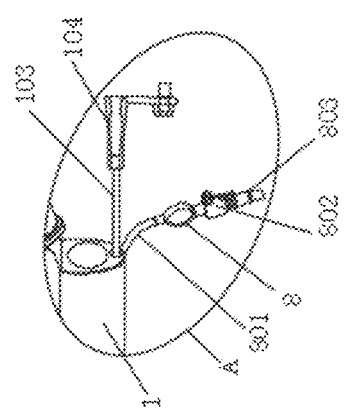
FIG. 4 is a close-up perspective view of the indicator balloon of FIG. 3, noted as section A in FIG. 3.

Referring particularly to FIG. 4, the lower portion of the inflation tube 103 is fluidically connected to an indication balloon 8 via a connecting tube 801. The indication balloon 8 is fixedly secured at a first end to the connecting tube 801, and fixedly secured at a second end to a valve connector 802. The valve connector 802 is removably secured to a one-way valve 803 at an opposing end to the connection to the indication balloon 8.

In use, a fiberoptic bronchoscope is inserted into the ventilation hole 6 and an endoscope is inserted into the drainage tube 2. The LMA is inserted into the esophageal opening of the patient, following the esophagus during insertion. The drainage tube 2 pushes the LMA into the esophageal tube of the patient, and the laryngeal tube for gastroscopy 1 disposed at the rear end of the laryngeal mask follows the esophageal tube into the esophagus of the patient.

After the LMA and the laryngeal tube for gastroscopy 1 are placed, a PC connector 201 is secured to the drainage tube 2 to connect the tube to an external monitoring device. The single-chamber joint 104 connects to an external inflation device. After the connection is completed, the inflation device is activated to allow the gas to enter the large balloon 3 and the small balloon 4 through the inflation tube 103 to inflate the large balloon 3 and the small balloon 4. During the inflation process, the amount of the gas filled stored within the large balloon 3 and the small balloon 4 is displayed on the indication balloon 8.

The inflated large balloon 3 and small balloon 4 seal the esophageal tube of the patient in the esophagus of the patient, and then the gastroscopy can be performed on the patient. Any secretions generated from the esophageal orifice of the patient during the gastroscopy is captured by and retained in the drainage tube 2. The suction hole 7 absorbs and cleans the secretions, thereby minimizing the phenomenon of coughing caused by secretions during the gastroscopy. After the endoscopy is finished, the check valve 803 is opened to release the fluid contents of the large balloon 3 and the small balloon 4. Then, the LMA and the laryngeal tube for gastroscopy 1 can be removed out from the esophageal tube of the patient.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A laryngeal mask airway configured for use in a gastroscopic procedure, the laryngeal mask airway comprising:

a laryngeal tube configured for use during a gastroscopy, the laryngeal tube including an outer surface, an inner surface, and a sidewall joining the outer surface and the inner surface, the inner surface defining a cavity therein, with a suction hole defined within the outer surface, and with an inflation tube hole defined within the sidewall;

an inflation tube including a first end received within the inflation tube hole of the laryngeal tube, and a second end connected to a single-cavity connector;

a drainage tube fixedly secured to the outer surface of the laryngeal tube, the drainage tube including a first end connected to a physical connection connector unit configured to connect the drainage tube to an external monitoring device, drainage tube defining a ventilation hole within an outer surface of an upper portion thereof;

a large balloon surrounding a middle portion of the laryngeal tube and the drainage tube; and a small balloon surrounding an end portion of the laryngeal tube and the draining tube, such that the small balloon is disposed opposite the single-cavity connector, wherein the laryngeal tube is configured to receive an airflow therein via the inflation tube to fill each of the large balloon and the small balloon to expand a volume of the laryngeal mask airway to secure the laryngeal mask airway within a patient's esophageal tube, and wherein the suction hole is configured to receive secretions from the patient's esophageal tube to minimize patient discomfort, and wherein the ventilation hole is configured to receive a fiberoptic bronchoscope therein to monitor breathing of the patient.

2. The laryngeal mask airway of claim 1, wherein the large balloon, the small balloon, and inflation tube form a closed fluid flow system.

3. The laryngeal mask airway of claim 1, further comprising a sealing belt secured to each opposing end of the large balloon to secure the large balloon to each of the laryngeal tube and the drainage tube.

4. The laryngeal mask airway of claim 1, further comprising a sealing belt secured to a non-terminal end of the small balloon, the non-terminal end disposed between a terminal end of the small balloon and the large balloon, the sealing belt configured to secure the small balloon to each of the laryngeal tube and the drainage tube.

5. The laryngeal mask airway of claim 1, wherein each of the ventilation hole and the suction hole are disposed between the large balloon and the small balloon.

6. The laryngeal mask airway of claim 1, further comprising an indication balloon secured at a first end to a connecting tube, the connecting tube received within the inflation tube hole, the indication balloon secured at a second end to a valve connector, the valve connector secured to a one-way valve, wherein the indication balloon is configured to receive an amount of air therein, and wherein the one-way valve is configured to display an amount of air within the system based on the amount of air received within the indication balloon.

7. The laryngeal mask airway of claim 1, wherein the drainage tube has a diameter of at least 14 mm.

8. The laryngeal mask airway of claim 1, wherein the outer surface of each of the drainage tube and the laryngeal tube includes a hydrophilic coating.

9. The laryngeal mask airway of claim 1, wherein the inner surface of the laryngeal tube and an inner surface of the drainage tube includes a hydrophilic coating.

\* \* \* \* \*